US012642639B2

(12) United States Patent
Perkins et al.

(10) Patent No.: US 12,642,639 B2
(45) Date of Patent: Jun. 2, 2026

(54) MODULAR STENT DEVICE FOR MULTIPLE VESSELS AND METHOD

(71) Applicant: Medtronic Vascular, Inc., Santa Rosa, CA (US)

(72) Inventors: Keith Perkins, Santa Rosa, CA (US); Zachary Borglin, Santa Rosa, CA (US); Mathew A. Haggard, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 323 days.

(21) Appl. No.: 17/691,716

(22) Filed: Mar. 10, 2022

(65) Prior Publication Data

US 2022/0192814 A1     Jun. 23, 2022

Related U.S. Application Data

(62) Division of application No. 16/367,889, filed on Mar. 28, 2019, now Pat. No. 11,304,794.

(Continued)

(51) Int. Cl.
*A61F 2/06*          (2013.01)
*A61F 2/07*          (2013.01)
(Continued)

(52) U.S. Cl.
CPC ................. *A61F 2/06* (2013.01); *A61F 2/07* (2013.01); *A61F 2/856* (2013.01); *A61F 2/954* (2013.01);
(Continued)

(58) Field of Classification Search
CPC .... A61F 2/06; A61F 2/07; A61F 2/856; A61F 2/954; A61F 2002/067; A61F 2250/0098;
(Continued)

(56) References Cited

U.S. PATENT DOCUMENTS 6,102,940 A     8/2000  Robichon et al.
6,641,606 B2   11/2003  Ouriel et al.
(Continued)

FOREIGN PATENT DOCUMENTS

EP        2525742 B1     11/2012
EP        2574306 A1      4/2013
(Continued)

OTHER PUBLICATIONS

European Patent Office Communication in Application No. 19 719 684.3, mailed Oct. 18, 2023, 5 pages.

(Continued)

*Primary Examiner* — Thomas McEvoy
(74) *Attorney, Agent, or Firm* — Brooks Kushman P.C.

(57)          ABSTRACT

The techniques of this disclosure generally relate to modular stent device and method of deploying the same. The method includes introducing a delivery system including the modular stent device via supra aortic access. The delivery system is advanced into the ascending aorta. Once positioned, the modular stent device is deployed from the delivery system such that an artery leg of the modular stent device engages the brachiocephalic artery and a bypass gate engages the aorta, wherein the artery leg partially collapses the bypass gate. The artery leg has a greater radial force than the bypass gate such that the artery leg remains un-collapsed and opened. Accordingly, blood flow through the artery leg and perfusion of the brachiocephalic artery and preservation of blood flow to cerebral territories including the brain is insured.

20 Claims, 9 Drawing Sheets

Related U.S. Application Data

(60) Provisional application No. 62/687,087, filed on Jun. 19, 2018.

(51) Int. Cl.
  *A61F 2/856* (2013.01)
  *A61F 2/954* (2013.01)

(52) U.S. Cl.
  CPC . *A61F 2002/067* (2013.01); *A61F 2250/0098* (2013.01)

(58) Field of Classification Search
  CPC .......... A61F 2002/061; A61F 2002/065; A61F 2002/826; A61F 2002/828; A61F 2/852
  See application file for complete search history.

(56) References Cited

U.S. PATENT DOCUMENTS

| | | | |
|---|---|---|---|
| 6,723,116 B2 | 4/2004 | Taheri | |
| 6,814,752 B1 | 11/2004 | Chuter | |
| 7,267,685 B2 | 9/2007 | Butaric et al. | |
| 8,545,549 B2 | 10/2013 | Hartley et al. | |
| 8,702,791 B2 | 4/2014 | Kelly | |
| 8,734,504 B2 | 5/2014 | Kelly | |
| 9,011,517 B2 | 4/2015 | Hartley et al. | |
| 9,101,456 B2 | 8/2015 | Hartley et al. | |
| 9,283,068 B2 | 3/2016 | Kelly | |
| 9,393,102 B2 | 7/2016 | Kelly | |
| 9,592,112 B2 | 3/2017 | Arbefeuille et al. | |
| 9,839,542 B2 | 12/2017 | Bruszewski et al. | |
| 9,861,505 B2 | 1/2018 | Khoury | |
| 9,949,818 B2 | 4/2018 | Kelly | |
| 9,980,832 B2 | 5/2018 | Kelly | |
| 9,993,330 B2 | 6/2018 | Roeder | |
| 10,231,822 B2 | 3/2019 | Hartley | |
| 2002/0058986 A1 | 5/2002 | Landau et al. | |
| 2002/0099441 A1 | 7/2002 | Dehdashtian | |
| 2003/0130720 A1 | 7/2003 | Depalma et al. | |
| 2003/0229389 A1* | 12/2003 | Escano | A61F 2/07 |
| | | | 623/1.13 |
| 2004/0117003 A1 | 6/2004 | Ouriel et al. | |
| 2005/0010277 A1 | 1/2005 | Chuter | |
| 2005/0102018 A1 | 5/2005 | Carpenter et al. | |
| 2006/0155363 A1 | 7/2006 | LaDuca et al. | |
| 2006/0184228 A1 | 8/2006 | Khoury | |
| 2007/0168013 A1 | 7/2007 | Douglas | |
| 2007/0250154 A1 | 10/2007 | Greenberg et al. | |
| 2008/0097578 A1 | 4/2008 | Erickson et al. | |
| 2008/0114441 A1* | 5/2008 | Rust | A61F 2/07 |
| | | | 623/1.13 |
| 2008/0147173 A1 | 6/2008 | Mciff et al. | |
| 2009/0043373 A1 | 2/2009 | Arnault De La Menardiere et al. | |
| 2009/0125100 A1 | 5/2009 | Mead | |
| 2009/0306763 A1 | 12/2009 | Roeder et al. | |
| 2010/0100168 A1 | 4/2010 | Chuter et al. | |
| 2011/0196477 A1 | 8/2011 | Ganesan et al. | |
| 2011/0238160 A1 | 9/2011 | Molony | |
| 2012/0123527 A1 | 5/2012 | Isch | |
| 2012/0271401 A1 | 10/2012 | Bruszewski et al. | |
| 2013/0013050 A1 | 1/2013 | Shalev et al. | |
| 2013/0013052 A1 | 1/2013 | Christiansen et al. | |
| 2013/0274861 A1 | 10/2013 | Kelly | |
| 2014/0172064 A1* | 6/2014 | Kelly | A61F 2/07 |
| | | | 623/1.13 |
| 2014/0316513 A1* | 10/2014 | Tang | A61F 2/852 |
| | | | 623/1.16 |
| 2016/0278910 A1* | 9/2016 | Kelly | A61F 2/07 |
| 2016/0287376 A1 | 10/2016 | Kelly | |
| 2016/0324626 A1 | 11/2016 | Kelly | |
| 2016/0367353 A1 | 12/2016 | Kelly | |
| 2017/0296324 A1 | 10/2017 | Argentine | |
| 2017/0319359 A1* | 11/2017 | Mehta | A61F 2/07 |
| 2017/0340461 A1 | 11/2017 | Varga | |
| 2018/0071077 A1 | 3/2018 | Argentine et al. | |
| 2018/0153677 A1 | 6/2018 | Perkins et al. | |
| 2018/0235786 A1 | 8/2018 | Kelly | |
| 2018/0243076 A1 | 8/2018 | Greenberg et al. | |
| 2018/0325653 A1 | 11/2018 | Kelly | |
| 2019/0380851 A1 | 12/2019 | Bertini et al. | |

FOREIGN PATENT DOCUMENTS

| | | |
|---|---|---|
| EP | 3448313 B1 | 4/2020 |
| WO | 2014163957 A1 | 10/2014 |
| WO | 2019245624 A1 | 12/2019 |

OTHER PUBLICATIONS

U.S. Appl. No. 16/502,462, of Keith Perkins et al., titled "Single Multibranch Stent Device Assembly and Method", filed Jul. 3, 2019.

U.S. Appl. No. 16/554,813, of Keith Perkins et al., titled "Modular Multibranch Stent Assembly and Method", filed Aug. 29, 2019.

U.S. Appl. No. 16/585,722, of Keith Perkins et al., titled "Docking Graft for Placement of Parallel Distally Extending Grafts Assembly and Method", filed Sep. 27, 2019.

U.S. Appl. No. 16/585,768, of Keith Perkins et al., titled "Supra Aortic Access Trifurcated Modular Stent Assembly and Method", filed Sep. 27, 2019.

U.S. Appl. No. 16/527,769, of Keith Perkins et al., titled "Modular Multibranch Stent Assembly and Method", filed Jul. 31, 2019.

U.S. Appl. No. 16/554,803, of Ashish Dhawan et al., titled "Use of Multiple Charged Ionic Compounds Derived From Polyamines for Waste Water Clarification", filed Aug. 29, 2019.

PCT/US2020/023170, The International Search Report and the Written Opinion of the International Searching Authority, mailed Jun. 30, 2020, 12 pages.

PCT/US2020/023176, The International Search Report and the Written Opinion of the International Searching Authority, mailed Jun. 19, 2020, 15 pages.

PCT/US2020/039169, The International Search Report and the Written Opinion of the International Searching Authority, mailed Oct. 5, 2020, 16 pages.

PCT/US2020/044833, The International Search Report and the Written Opinion of the International Searching Authority, mailed Nov. 16, 2020, 11 pages.

International Search Report, Application No. PCT/US2019/024676, Jun. 17, 2019, pp. 1-14.

M. Lachat, "Nexus aortic arch stentgraft: Mid-term results", Leipzig Interventional Course 2017, UniversitatsSpital Zurich, Jan. 24-27, 2017, pp. 1-30, www.leipzig-interventional-course.com.

Jae Woong Lim et al., "Totally endocascular aortic arch repair by branched stent graft placement", Journal of Vascular Surgery Cases, Dec. 2015, pp. 279-282, vol. 1, No. 4.

N. Anthony Lee, Md., "The Bolton Medical Branched Thoracic Stent-Graft", Sponsored by Bolton Medical, Inc., pp. 1-6.

Michael D. Dake et al., "Thoracic Branch Endoprosthesis: Early Case Experience and the Clinical Trial", Supplement to Endovascular Today, Mar. 2017, pp. 21-24, vol. 16, No. 3.

Augusto D'Onofrio et al., "Endovascular treatment of aortic arch aneurysm with a single-branched double-stage stent graft", The Journal of Thoracic and Cardiovascular Surgery, Jul. 11, 2017, pp. e75-e77, vol. 154, No. 5.

Joseph Anderson, "Complete endovascular debranching of the aortic arch: A report of two cases", Vascular, Jul. 11, 2014, pp. 1-7, http://vas.sagepub.com/content/early/2014/07/11/1708538114542174, SAGE Publications.

Ciro Ferrer et al., "Endovascular repair of aortic arch disease with double inner branched thoracic stent graft: the Bolton perspective", The Journal of Cardiovascular Surgery, Aug. 2018, pp. 547-553, vol. 59 No. 4.

Stephan Haulon et al., "Global experience with an inner branched arch endograft", The Journal of Thoracic and Cardiovascular Surgery, 2014, pp. 1709-1716, vol. 148 No. 4.

Chen Huang et al., "Application of Unibody Single-Branch Endografts in Stanford Type B Dissections with Primary Entry Tear Adjacent to the Left Subclavian Artery: A Computed TomographyeBased Plan-

(56) References Cited

OTHER PUBLICATIONS ning Study", Annals for Vascular Surgery, Aug. 2015, pp. 1174-1180, vol. 29 No. 6.

Himanshu J. Patel et al., "Branched Endovascular Therapy of the Distal Aortic Arch: Preliminary Results of the Feasibility Multicenter Trial of the Gore Thoracic Branch Endoprosthesis", Branched Aortic Arch Tevar Trial, The Society of Thoracic Surgeons, Mar. 22, 2016, pp. 1190-1198, Elsevier Lid.

Vincent Riambau et al., "Application of the Bolton Relay Device for Thoracic Endografting In or Near the Aortic Arch", Aorta, Feb. 2015, pp. 16-24, vol. 3 Issue 1, Science International Corp., http://aorta.scienceinternational.org.

R. Spear et al., "Editor's Choice e Subsequent Results for Arch Aneurysm Repair with Inner Branched Endografts", Arch Aneurysm Endovascular Repair, Dec. 8, 2015, pp. 380-385, European Society for Vascular Surgery, Elsevier Ltd.

R. Spear et al., "Complex endovascular repair of postdissection arch and thoracoabdominal aneurysms", Society for Vascular Surgery, Journal of Vascular Surgery, Sep. 5, 2017, pp. 1-8, Elsevier Inc.

R. Spear et al., "Total Endovascular Treatment of Aortic Arch Disease Using an Arch Endograft With 3 Inner Branches", Journal of Endovascular Therapy, 2017, pp. 534-538, vol. 24(4), Sage Publications.

Zhong Gao Wang, "Single-Branch Endograft for Treating Stanford Type B Aortic Dissections With Entry Tears in Proximity to the Left Subclavian Artery", J Endovasc Ther, 2005, pp. 588-593, International Society of Endovascular Specialists.

U.S. Appl. No. 62/430,218, of Keith Perkins et al., titled "Modular Aortic Arch Prosthetic Assembly and Method of Use Thereof", filed Dec. 5, 2016.

U.S. Appl. No. 62/687,087, of Keith Perkins et al., titled "Modular Stent Device for Multiple Vessels", filed Jun. 19, 2018.

U.S. Appl. No. 15/830,221, of Keith Perkins et al., titled "Modular Aortic Arch Prosthetic Assembly and Method of Use Thereof", filed Dec. 4, 2017.

U.S. Appl. No. 16/367,906, of Keith Perkins et al., titled "Supra Aortic Access Modular Stent Assembly and Method", filed Mar. 28, 2019.

U.S. Appl. No. 16/367,922, of Keith Perkins et al., titlled "Femoral Aortic Access Modular Stent Assembly and Method", filed Mar. 28, 2019.

* cited by examiner

MODULAR STENT DEVICE FOR MULTIPLE VESSELS AND METHOD

CROSS-REFERENCE TO RELATED APPLICATIONS

This application is a divisional of pending U.S. patent application Ser. No. 16/367,889, entitled "MODULAR STENT DEVICE FOR MULTIPLE VESSELS AND METHOD", filed Mar. 28, 2019, and issued as U.S. Pat. No. 11,304,794 on Apr. 19, 2022, which claims the benefit of U.S. Provisional Application No. 62/687,087, filed on Jun. 19, 2018, entitled "MODULAR STENT DEVICE FOR MULTIPLE VESSELS" of Perkins et al., which are incorporated herein by reference in their entirety.

FIELD

The present technology is generally related to an intra-vascular device and method. More particularly, the present application relates to a device for treatment of intra-vascular diseases.

BACKGROUND

Aneurysms, dissections, penetrating ulcers, intramural hematomas and/or transections may occur in blood vessels, and most typically occur in the aorta and peripheral arteries. The diseased region of the aorta may extend into areas having vessel bifurcations or segments of the aorta from which smaller "branch" arteries extend.

The diseased region of the aorta can be bypassed by use of a stent-graft placed inside the vessel spanning the diseased portion of the aorta, to seal off the diseased portion from further exposure to blood flowing through the aorta.

The use of stent-grafts to internally bypass the diseased portion of the aorta is not without challenges. In particular, care must be taken so that critical branch arteries are not covered or occluded by the stent-graft yet the stent-graft must seal against the aorta wall and provide a flow conduit for blood to flow past the diseased portion.

SUMMARY

The techniques of this disclosure generally relate to modular stent device and method of deploying the same. The method includes introducing a delivery system including the modular stent device via supra aortic access. The modular stent device includes a main body having a first longitudinal axis, a bypass gate having a second longitudinal axis, and an artery leg having a third longitudinal axis. The first, second, and third longitudinal axes are parallel with one another when the modular stent device is in a relaxed configuration.

The delivery system is advanced into the ascending aorta. Once positioned, the modular stent device is deployed from the delivery system such that the artery leg of the modular stent device engages the brachiocephalic artery and the bypass gate engages the aorta, wherein the artery leg partially collapses the bypass gate.

The artery leg has a greater radial force than the bypass gate such that the artery leg remains un-collapsed and opened. Accordingly, blood flow through the artery leg and perfusion of the brachiocephalic artery and preservation of blood flow to cerebral territories including the brain is insured.

In one aspect, the present disclosure provides an assembly including a modular stent device including a main body, a bypass gate extending distally from a distal end of the main body, and an artery leg extending distally from the distal end of the main body, wherein the artery leg has a greater radial force than a radial force of the bypass gate. The main body has a first longitudinal axis, the bypass gate has a second longitudinal axis, and the artery leg has a third longitudinal axis. The first, second, and third longitudinal axes are parallel with one another when the modular stent device is in a relaxed configuration.

In another aspect, the present disclosure provides a method including introducing a delivery system including a modular stent device via femoral access. The modular stent device includes a main body having a first longitudinal axis, a bypass gate having a second longitudinal axis, and an artery leg having a third longitudinal axis. The first, second, and third longitudinal axes are parallel with one another when the modular stent device is in a relaxed configuration.

The delivery system is advanced into the ascending aorta. The modular stent device is deployed from the delivery system such that a distal opening of the artery leg of the modular stent device is proximal to the brachiocephalic artery and the bypass gate of the modular stent device engages the aorta, wherein the artery leg partially collapses the bypass gate.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
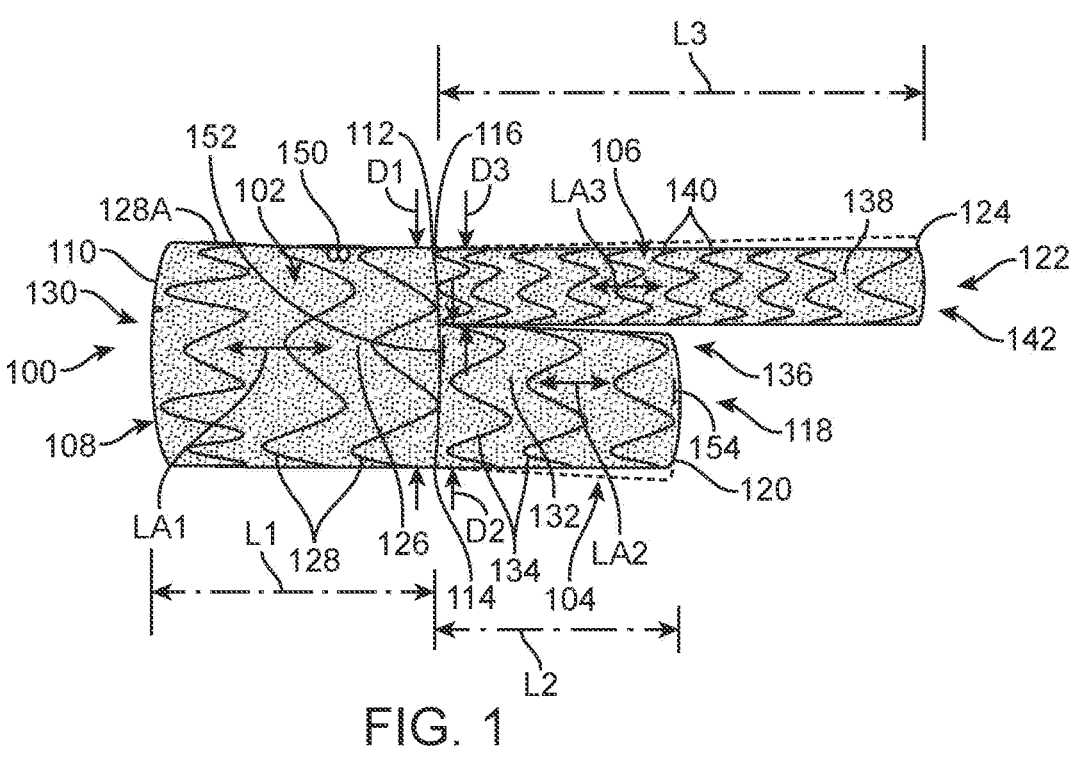
FIG. 1 is a side plan view of a modular stent device in accordance with one embodiment.
Figure 2:
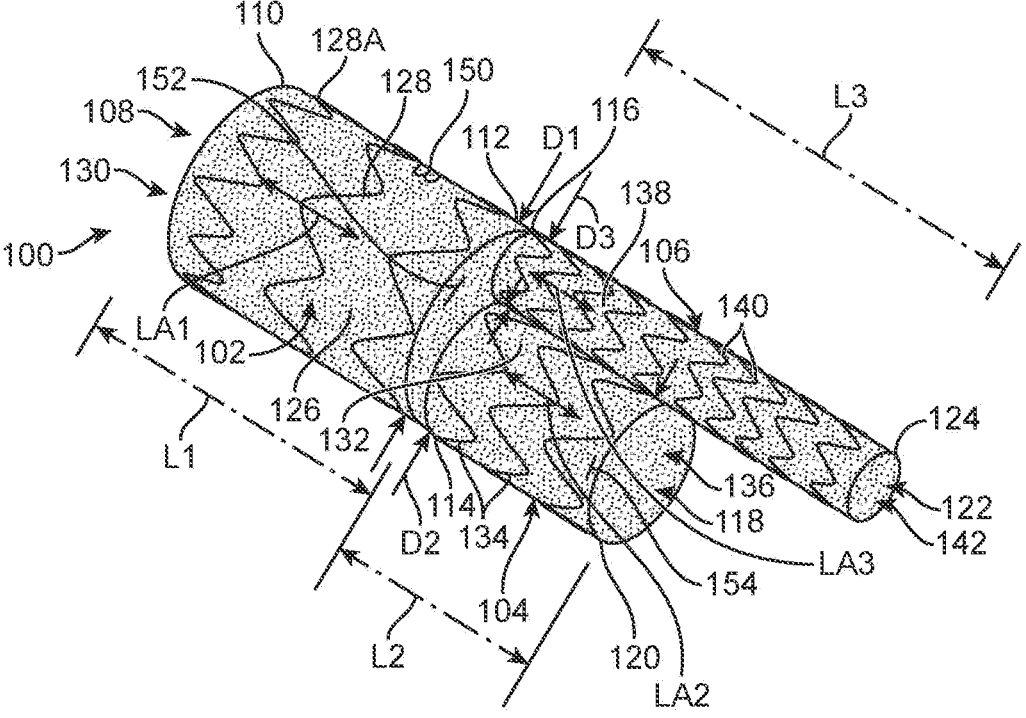
FIG. 2 is a perspective view of the modular stent device of FIG. 1 in accordance with one embodiment.

FIG. 1 is a side plan view of a modular stent device 100 in accordance with one embodiment. FIG. 2 is a perspective view of modular stent device 100 of FIG. 1 in accordance with one embodiment.

Referring now to FIGS. 1 and 2 together, modular stent device 100, sometimes called a prosthesis or aortic arch prosthesis, includes a main body 102, a bypass gate 104 and an artery leg 106, sometimes called a brachiocephalic artery (BCA) leg/limb 106.

In accordance with this embodiment, main body 102 includes a main body proximal opening 108 at a proximal end 110 of main body 102. A distal end 112 of main body 102 is coupled to a proximal end 114 of bypass gate 104 and a proximal end 116 of artery leg 106.

Bypass gate 104 includes a bypass gate distal opening 118 at a distal end 120 of bypass gate 104. Artery leg 106 includes a leg distal opening 122 at a distal end 124 of artery leg 106. Openings 118, 122 are sometime called distal first and second openings 118, 122, respectively.

As used herein, the proximal end of a prosthesis such as modular stent device 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of modular stent device 100 is the end nearest the operator (the end nearest the handle), i.e., the distal end of the catheter and the proximal end of modular stent device 100 are the ends furthest from the handle while the proximal end of the catheter and the distal end of modular stent device 100 are the ends nearest the handle. However, those of skill in the art will understand that depending upon the access location, modular stent device 100 and the delivery system descriptions may be consistent or opposite in actual usage.

Main body 102 includes graft material 126 and one or more circumferential stents 128 coupled to graft material 126. Graft material 126 may be any suitable graft material, for example and not limited to, woven polyester, DACRON® material, expanded polytetrafluoroethylene, polyurethane, silicone, electro spun materials, or other suitable materials.

Circumferential stents 128 may be coupled to graft material 126 using stitching or other means. In the embodiment shown in FIGS. 1 and 2, circumferential stents 128 are coupled to an outside surface of graft material 126. However, circumferential stents 128 may alternatively be coupled to an inside surface of graft material 126.

Although shown with a particular number of circumferential stents 128, in light of this disclosure, those of skill in the art will understand that main body 102 may include a greater or smaller number of stents 128, e.g., depending upon the desired length of main body 102 and/or the intended application thereof.

Circumferential stents 128 may be any stent material or configuration. As shown, circumferential stents 128, e.g., self-expanding members, are preferably made from a shape memory material, such as nickel-titanium alloy (nitinol), and are formed into a zig-zag configuration. The configuration of circumferential stents 128 is merely exemplary, and circumferential stents 128 may have any suitable configuration, including but not limiting to a continuous or non-continuous helical configuration. In another embodiment, circumferential stents 128 are balloon expandable stents.

The circumferential stent 128A of the circumferential stents 128 which is disposed at proximal end 110 is referred to herein as the proximal-most stent 128A. In the embodiment of FIGS. 1 and 2, proximal-most stent 128A extends only to the edge of graft material 126 in a closed-web configuration as shown. However, in another embodiment, proximal-most stent 128A extends proximally past the edge of graft material 126 in an open-web or uncovered configuration.

Further, main body 102 includes a longitudinal axis LA1. A lumen 130 is defined by graft material 126, and generally by main body 102. Lumen 130 extends generally parallel to longitudinal axis LA1 and between proximal opening 108 and distal end 112 of main body 102. Graft material 126 is cylindrical having a substantially uniform diameter in this embodiment. However, in other embodiments, graft material 126 varies in diameter.

Bypass gate 104 includes graft material 132 and one or more circumferential stents 134 coupled to graft material 132. Graft material 132 may be any suitable graft material, for example and not limited to, woven polyester, DACRON® material, expanded polytetrafluoroethylene, polyurethane, silicone, electro spun materials, or other suitable materials.

Circumferential stents 134 may be coupled to graft material 132 using stitching or other means. In the embodiment shown in FIGS. 1 and 2, circumferential stents 134 are coupled to an outside surface of graft material 132. However, circumferential stents 134 may alternatively be coupled to an inside surface of graft material 132.

Although shown with a particular number of circumferential stents 134, in light of this disclosure, those of skill in the art will understand that bypass gate 104 may include a greater or smaller number of stents 134, e.g., depending upon the desired length of bypass gate 104 and/or the intended application thereof.

Circumferential stents 134 may be any stent material or configuration. As shown, circumferential stents 110, e.g., self-expanding members, are preferably made from a shape memory material, such as nickel-titanium alloy (nitinol), and are formed into a zig-zag configuration. The configuration of circumferential stents 134 is merely exemplary, and circumferential stents 134 may have any suitable configuration, including but not limiting to a continuous or non-continuous helical configuration. In another embodiment, circumferential stents 134 are balloon expandable stents.

Further, bypass gate 104 includes a longitudinal axis LA2. A lumen 136 is defined by graft material 132, and generally by bypass gate 104. Lumen 136 extends generally parallel to longitudinal axis LA2 and between proximal end 114 and distal opening 118 of bypass gate 104. Graft material 132 is cylindrical having a substantially uniform diameter in this embodiment. However, in other embodiments, graft material 132 varies in diameter.

Artery leg 106 includes graft material 138 and one or more circumferential stents 140 coupled to graft material 138. Graft material 138 may be any suitable graft material, for example and not limited to, woven polyester, DACRON® material, expanded polytetrafluoroethylene, polyurethane, silicone, electro spun materials, or other suitable materials.

Circumferential stents 140 may be coupled to graft material 138 using stitching or other means. In the embodiment shown in FIGS. 1 and 2, circumferential stents 140 are coupled to an outside surface of graft material 138. However, circumferential stents 140 may alternatively be coupled to an inside surface of graft material 138.

Although shown with a particular number of circumferential stents 140, in light of this disclosure, those of skill in the art will understand that artery leg 106 may include a greater or smaller number of stents 140, e.g., depending upon the desired length of artery leg 106 and/or the intended application thereof.

Circumferential stents 140 may be any stent material or configuration. As shown, circumferential stents 140, e.g., self-expanding members, are preferably made from a shape memory material, such as nickel-titanium alloy (nitinol), and are formed into a zig-zag configuration. The configuration of circumferential stents 140 is merely exemplary, and circumferential stents 140 may have any suitable configuration, including but not limiting to a continuous or non-continuous helical configuration. In another embodiment, circumferential stents 140 are balloon expandable stents.

Further, artery leg 106 includes a longitudinal axis LA3. A lumen 142 is defined by graft material 138, and generally by artery leg 106. Lumen 142 extends generally parallel to longitudinal axis LA3 and between proximal end 116 and distal opening 122 of artery leg 106. Graft material 138 is cylindrical having a substantially uniform diameter in this embodiment. However, in other embodiments, graft material 138 varies in diameter.

Generally, main body 102 is bifurcated at distal end 112 into bypass gate 104 and artery leg 106. More particularly, lumen 130 of main body 102 is bifurcated into lumen 136 of bypass gate 104 and lumen 142 of artery leg 106.

In one embodiment, graft materials 126, 132, 138 may be the same graft material, e.g., may be a single piece of graft material cut and sewn. However, in other embodiments, one or more of graft materials 126, 132, 138 may be different that the others of graft materials 126, 132, 138, e.g., different graft materials are cut and sewn together. In the relaxed configuration of modular stent device 100 as illustrated in FIGS. 1 and 2, longitudinal axes LA1, LA2, and LA3 are parallel with one another such that bypass gate 104 and artery leg 106 extend distally from main body 102.

Main body 102 has a first diameter D1, bypass gate 104 has a second diameter D2, and artery leg 106 has a third diameter D3. In accordance with this embodiment, first diameter D1 is greater than second diameter D2. Further, second diameter D2 is greater than third diameter D3. In accordance with this embodiment, first diameter D1 is greater than second diameter D2 combined with third diameter D3 (D1>D2+D3) such that bypass gate 104 and artery leg 106 are located within an imaginary cylinder defined by graft material 126 of main body 102 extended in the distal direction. The parallel design mimics anatomical blood vessel bifurcations to limit flow disruptions.

In one embodiment, first diameter D1 is greater than second diameter D2 combined with third diameter D3 (D1>D2+D3) at distal end 112 and proximal ends 114, 116, sometimes called the transition region. However, main body 102, bypass gate 104 and/or artery leg 106, flare or taper away from the transition region in accordance with another embodiment, so D1>D2+D3 at the transition region but is not necessarily correct in regions away from the transition region. Flaring is indicated by the dashed lines in FIG. 1.

Stated another way, the transition region from main body 102 to artery leg 106 and bypass gate 104 does not exceed first diameter D1 of main body 102. This insures artery leg 106 and bypass gate 104 don't crush each other or negatively impact flow in any way. By avoiding having artery leg 106 and bypass gate 104 extend out wider than main body 102, a good seal of stents 128 of main body 102 against the aorta is insured and type I endoleaks are minimized or avoided.

In accordance with one embodiment, the transition region between main body 102 and artery leg 106 and bypass gate 104 is fully supported by one or more supporting stents, e.g., stents 128, 134, 140, to prevent kinking in angled anatomy. Absent the supporting stents, modular stent device 100 may be predispose to kinking in type III arches or gothic arches.

Main body 102 has a first length L1 in a direction parallel to the longitudinal axis LA1, bypass gate 104 has a second length L2 in a direction parallel to the longitudinal axis LA2, and artery leg 106 has a third length L3 in a direction parallel to the longitudinal axis LA3. In accordance with this embodiment, third length L3 is greater than second length L2 such that distal opening 122 the artery leg 106 is distal to distal opening 118 of bypass gate 104. Generally, artery leg 106 is longer than bypass gate 104.

In one embodiment, first diameter D1 ranges from 26 mm to 54 mm. In another embodiment, first diameter D1 is smaller for a second device to treat the left common carotid or left subclavian artery and first diameter D1 is as small as 22 mm for transections. In one particular embodiment, first diameter D1 is in the range of 20 mm to 60 mm.

In one embodiment, second diameter D2 is any one of a number of values to accommodate a minimum diameter of artery leg 106 and the various possible diameters D1 of main body 102. In one embodiment, second diameter D2 of bypass gate 104 is maximized by subtracting the third diameter D3 of artery leg 106 from first diameter D1 of main body 102. For the brachiocephalic artery, also known as the innominate artery, the minimum diameter of artery leg 106 is suitably around 10 mm to 14 mm. Accordingly, when first diameter D1 is 20 mm, second diameter D2 of bypass gate 104 is 10 mm. However, second diameter D2 is as large as 50 mm in another embodiment. Suitably, second diameter D2 is in the approximate range of 10 mm to 46 mm.

Third diameter D3 is the diameter for the innominate artery, the left subclavian, and/or the left common carotid in one embodiment. The innominate artery ranges in size from approximately 10 mm up to 24 mm. The left subclavian artery size range is closer to 8 mm to 14 mm and the left common carotid artery is in the 6 mm to 10 mm range. Accordingly, third diameter D3 is suitably in the approximate range of 6 mm to 24 mm and in one particular embodiment is in the approximate range of 5 mm to 22 mm.

In one embodiment, landing is targeted in the middle of the ascending aorta. The distance between the sinotubular junction STJ and innominate artery ranges in size from 4-8 cm so first length L1 is suitably in the range of around 4 cm to 8 cm. However, to extend coverage all the way to the sinotubular junction STJ, in one embodiment, first length L1 can vary. Suitably, first length L1 is in the approximate range of 10 mm to 160 mm. Alternatively, a proximal cuff is used as discussed further below.

Second length L2 is suitably sufficient for providing adequate overlap in an environment with significant respiratory and cardiac induced motion. It is also suitable to space bypass gate 104 so that bypass gate 104 does not inadvertently open inside of a target branch. In one embodiment, second length L2 is suitably in the approximate range of 10 mm to 240 mm and in one particular embodiment is in the range of 20 mm to 70 mm. In one embodiment, the minimum overlap is shortened by providing some mechanism for anchoring of the device.

Third length L3 is suitably in the approximate range of 30 mm to 400 mm in one embodiment and is in the range of 20 mm to 180 mm in one particular embodiment. In one embodiment, artery leg 106 is extended with additional devices.

Although fixed diameters D1, D2, and D3 are illustrated and discussed, in one embodiment, main body 102, bypass gate 104 and/or artery leg 106 are non-uniform in diameter. For example, main body 102 flares or tapers at proximal end 110. Similarly, bypass gate 104 and/or artery leg 106 flare or taper at distal ends 120, 124, respectively. For example, bypass gate 104 and/or artery leg 106 flare or taper at distal ends 120, 124 to enhance sealing.

Artery leg 106 is configured to exert a higher radial force than the radial force of bypass gate 104. As used herein, "radial force" includes both a radial force exerted during expansion/deployment as well as a chronic radial force continuously exerted after implantation such that a scaffold has a predetermined compliance or resistance as the surrounding native anatomy, e.g., the aorta, expands and contracts during the cardiac cycle. The radial force of bypass gate 104 is configured to be lower than that of artery leg 106 to avoid collapse of artery leg 106 when bypass gate 104 is deployed against and adjacent thereof and thus maintain perfusion of the brachiocephalic artery as discussed further below.

To configure bypass gate 104 and artery leg 106 with differing relative radial forces, circumferential stents 140 of artery leg 106 be constructed with relatively thicker and/or shorter segments of material than circumferential stents 134 of bypass gate 104. Shorter and/or thicker circumferential stents 140 have less flexibility but greater radial force to ensure that circumferential stents 134 of bypass gate 104 do not collapse lumen 142 of artery leg 106. Other variations or modification of circumferential stents 134, 140 may be used to achieve relative radial forces in other embodiments.

Modular stent device 100 further includes radiopaque markers 150, 152, 154. In accordance with this embodiment, radiopaque marker 150 is shaped as a figure 8 marker, i.e., in the shape of the number 8. Radiopaque marker 150 is sewn into graft material 126 in line with artery leg 106. Under fluoroscopy, radiopaque marker 150 is rotated so that it is seen on the edge on the outer curvature of the aortic arch in one embodiment so that artery leg 106 is accurately and reproducibly deployed on the outer curve of the aorta.

Radiopaque maker 152 is sewn in the transition region where main body 102 meets bypass gate 104 and artery leg 106 to indicate the desired extent of overlap. Radiopaque marker 154, e.g., a coil marker, is sewn into bypass gate 104 to aid in cannulation of bypass gate 104.

Figures 3, 4:
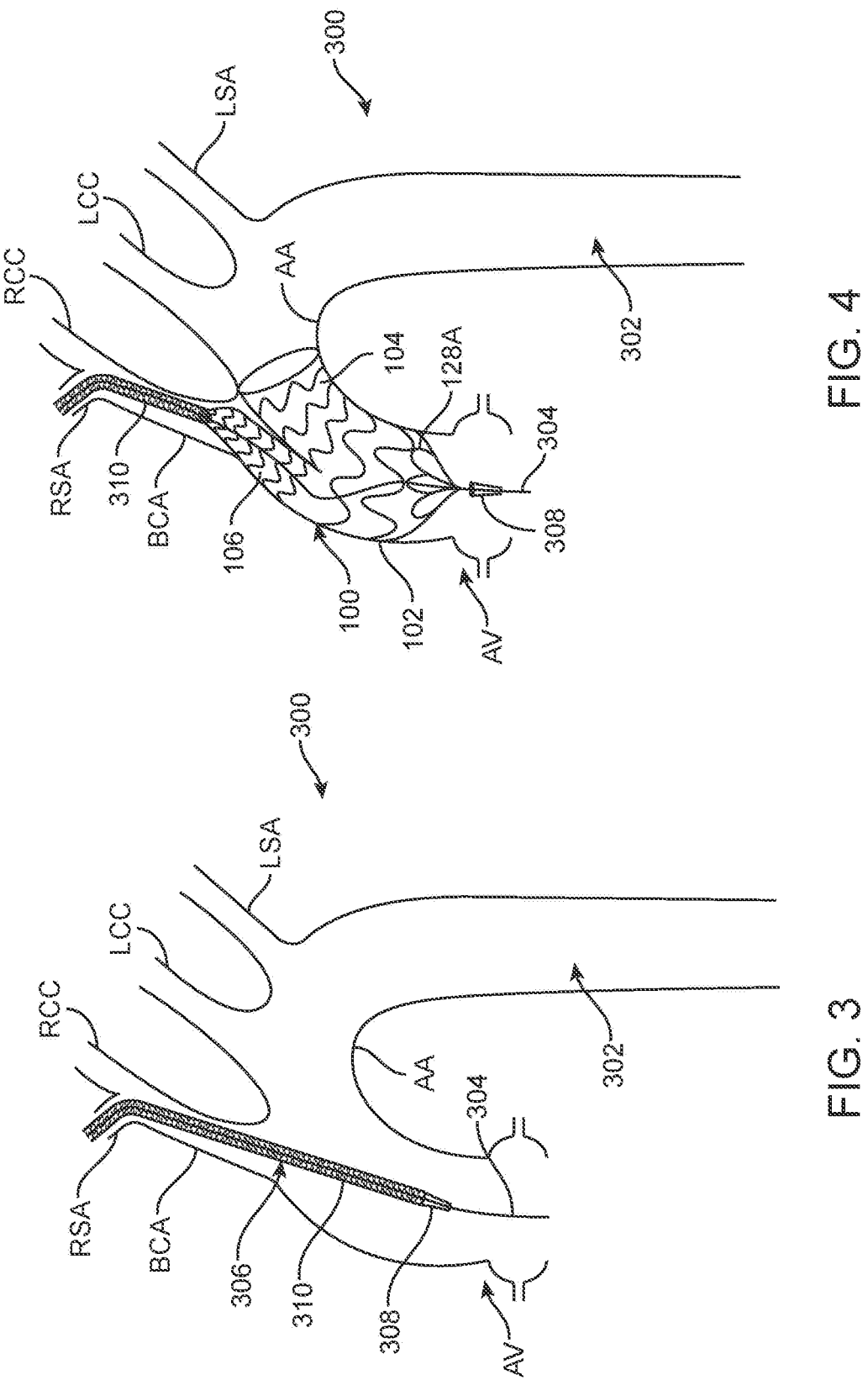
FIG. 3 is a cross-sectional view of a vessel assembly including the modular stent device of FIGS. 1 and 2 during deployment in accordance with one embodiment.
FIG. 4 is a cross-sectional view of the vessel assembly of FIG. 3 at a later stage during deployment of the modular stent device in accordance with one embodiment.

FIG. 3 is a cross-sectional view of a vessel assembly 300 including modular stent device 100 of FIGS. 1 and 2 during deployment in accordance with one embodiment. Referring to FIGS. 1, 2 and 3 together, the thoracic aorta 302 has numerous arterial branches. The arch AA of the aorta 302 has three major branches extending therefrom, all of which usually arise from the convex upper surface of the arch AA. The brachiocephalic artery BCA originates anterior to the trachea. The brachiocephalic artery BCA divides into two branches, the right subclavian artery RSA (which supplies blood to the right arm) and the right common carotid artery RCC (which supplies blood to the right side of the head and neck). The left common carotid artery LCC artery arises from the arch AA of the aorta 302 just to the left of the origin of the brachiocephalic artery BCA. The left common carotid artery LCC supplies blood to the left side of the head and neck. The third branch arising from the aortic arch AA, the left subclavian artery LSA, originates behind and just to the left of the origin of the left common carotid artery LCC and supplies blood to the left arm.

However, a significant proportion of the population has only two great branch vessels coming off the aortic arch AA while others have four great branch vessels coming of the aortic arch AA. Accordingly, although a particular anatomical geometry of the aortic arch AA is illustrated and discussed, in light of this disclosure, those of skill in the art will understand that the geometry of the aortic arch AA has anatomical variations and that the various structures as disclosed herein would be modified accordingly.

Aneurysms, dissections, penetrating ulcers, intramural hematomas and/or transections, generally referred to as a diseased region of the aorta 302, may occur in the aorta arch AA and the peripheral arteries BCA, LCC, LSA. For example, thoracic aortic aneurysms include aneurysms present in the ascending thoracic aorta, the aortic arch AA, and one or more of the branch arteries BCA, LCC, LSA that emanate therefrom. Thoracic aortic aneurysms also include aneurysms present in the descending thoracic aorta and branch arteries that emanate therefrom. Accordingly, the aorta 302 as illustrated in FIG. 3 has a diseased region similar to any one of those discussed above which will be bypassed and excluded using modular stent device 100 as discussed below.

As illustrated in FIG. 3, a guide wire 304 is introduced via supra aortic access, e.g. through the right subclavian artery RSA, and advanced into the ascending aorta 302. A delivery system 306 including modular stent device 100 is introduced via supra aortic access, e.g. through the right subclavian artery RSA, and is advanced into the ascending aorta 302 over guidewire 304. Delivery system 306 is positioned at the desired location such that the position of modular stent device 100 is in the ascending aorta near the aortic valve AV.

In accordance with this embodiment, delivery system 306 includes a tip capture mechanism 308 and a delivery sheath 310. Delivery sheath 310 maintains modular stent device 100 in a collapsed configuration during delivery to the desired location within the aorta 302. Tip capture mechanism 308 captures proximal end 110 of main body 102, e.g., proximal circumferential stent 128A, and keeps proximal end 110 in a collapsed configuration until released as discussed further below. Tip capture mechanism 308 controls proximal deployment accuracy in a highly mobile environment with large amounts of fluid flow, e.g., in the ascending aorta.

FIG. 4 is a cross-sectional view of vessel assembly 300 of FIG. 3 at a later stage during deployment of modular stent device 100 in accordance with one embodiment. Referring to FIGS. 3 and 4 together, delivery sheath 310 is withdrawn to expose main body 102, bypass gate 104, and the proximal most portion of artery leg 106. This deploys main body 102 and bypass gate 104 which self-expand into the aorta 302. Bypass gate 104 is opened thus insuring perfusion to distal territories, e.g., including the aorta 302, the left common carotid LCC, and the left subclavian artery LCA. Radiopaque marker 150 aids in positioning of modular stent device 100 during deployment.

The design of bypass gate 104 limits wind socking of modular stent device 100 during deployment. More particularly, the relatively large diameter D2 of bypass gate 104 readily allows blood flow through bypass gate 104 thus minimizing undesirable motion of modular stent device 100 during deployment.

To allow adjustment of the position of modular stent device 100, proximal end 110 of main body 102 remains captured within tip capture mechanism 308 and the distal portion of artery leg 106 remains collapsed and captured within delivery sheath 310. Modular stent device 100 is moved, e.g., proximally or distally and/or rotated, if necessary, until positioned at the desired location. The closed web tip capture system of tip capture mechanism 308 insures accurate deployment at the sinotubular junction STJ to maximize the proximal seal of modular stent device 100 in the aorta 302.

Figures 5, 6:
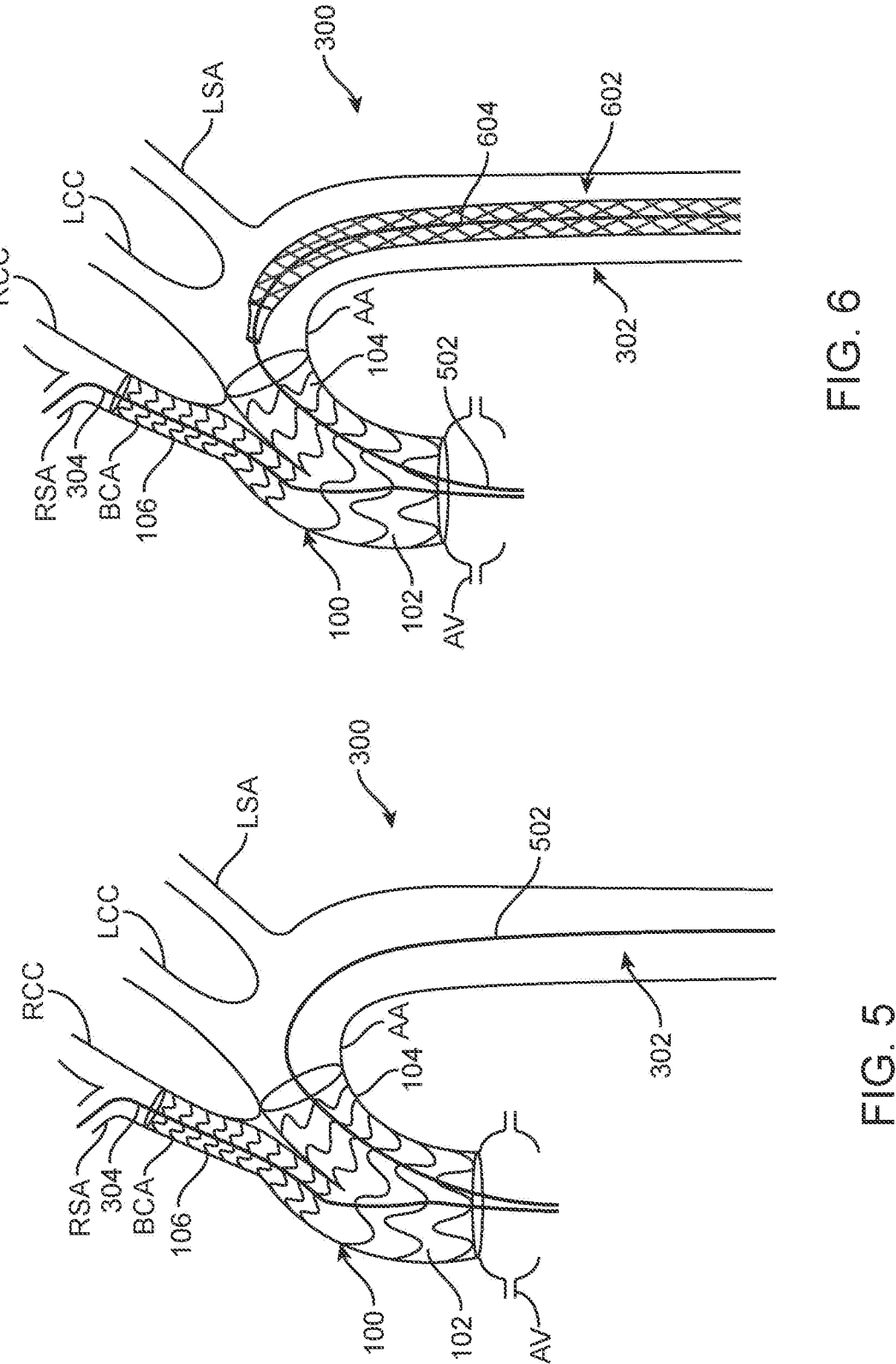
FIG. 5 is a cross-sectional view of the vessel assembly of FIG. 4 at a later stage during deployment of the modular stent device in accordance with one embodiment.
FIG. 6 is a cross-sectional view of the vessel assembly of FIG. 5 at a later stage during deployment of a tube graft into the modular stent device in accordance with one embodiment.

FIG. 5 is a cross-sectional view of vessel assembly 300 of FIG. 4 at a later stage during deployment of modular stent device 100 in accordance with one embodiment. Referring to FIGS. 4 and 5 together, delivery sheath 310 is completely withdrawn to expose the entirety of artery leg 106. This deploys artery leg 106 which expands into the brachiocephalic artery BCA. Further, proximal end 110 of main body 102 is released from tip capture mechanism 308 and thus expands into aorta 302. Generally, this completes deployment of modular stent device 100.

As artery leg 106 has a greater radial force than bypass gate 104, artery leg 106 remains un-collapsed and opened. Accordingly, blood flow through artery leg 106 and perfusion of the brachiocephalic artery BCA and preservation of blood flow to cerebral territories including the brain is insured. This avoids stroke, or other medical complications from occlusion of the brachiocephalic artery BCA.

Perfusion of the brachiocephalic artery BCA is immediate and dependable. More particularly, artery leg 106 is released within brachiocephalic artery BCA and accordingly is necessarily located therein. Artery leg 106 is located within brachiocephalic artery BCA regardless of the radial orientation or longitudinal (axial) placement of modular stent device 100 within the aorta 302. By avoiding the requirement of precise radial orientation and longitudinal placement of modular stent device 100, the complexity of the procedure of deploying modular stent device 100 is reduced thus insuring the most possible favorable outcome.

If there is any collapse between artery leg 106 and bypass gate 104, the collapse is in bypass gate 104. However, bypass gate 104 has a sufficiently large diameter D2 such that any collapse of bypass gate 104 is partial and blood flow through bypass gate 104 and the aorta 302 is maintained.

Referring now just to FIG. 5, a second guidewire 502 is advanced into and through bypass gate 102. Bypass gate 102 is cannulated from the femoral artery or in conjunction with the left subclavian artery LSA. In one particular embodiment, second guidewire 502 is inserted into the femoral artery and routed up through the abdominal aorta, and into the thoracic aorta.

FIG. 6 is a cross-sectional view of vessel assembly 300 of FIG. 5 at a later stage during deployment of a tube graft 702 (see FIG. 7) into modular stent device 100 in accordance with one embodiment. Referring to FIGS. 5 and 6 together, a tube graft delivery system 602 is advanced over second guidewire 502 and into bypass gate 104. Tube graft delivery system 602 includes a sheath 604.

Figure 7:
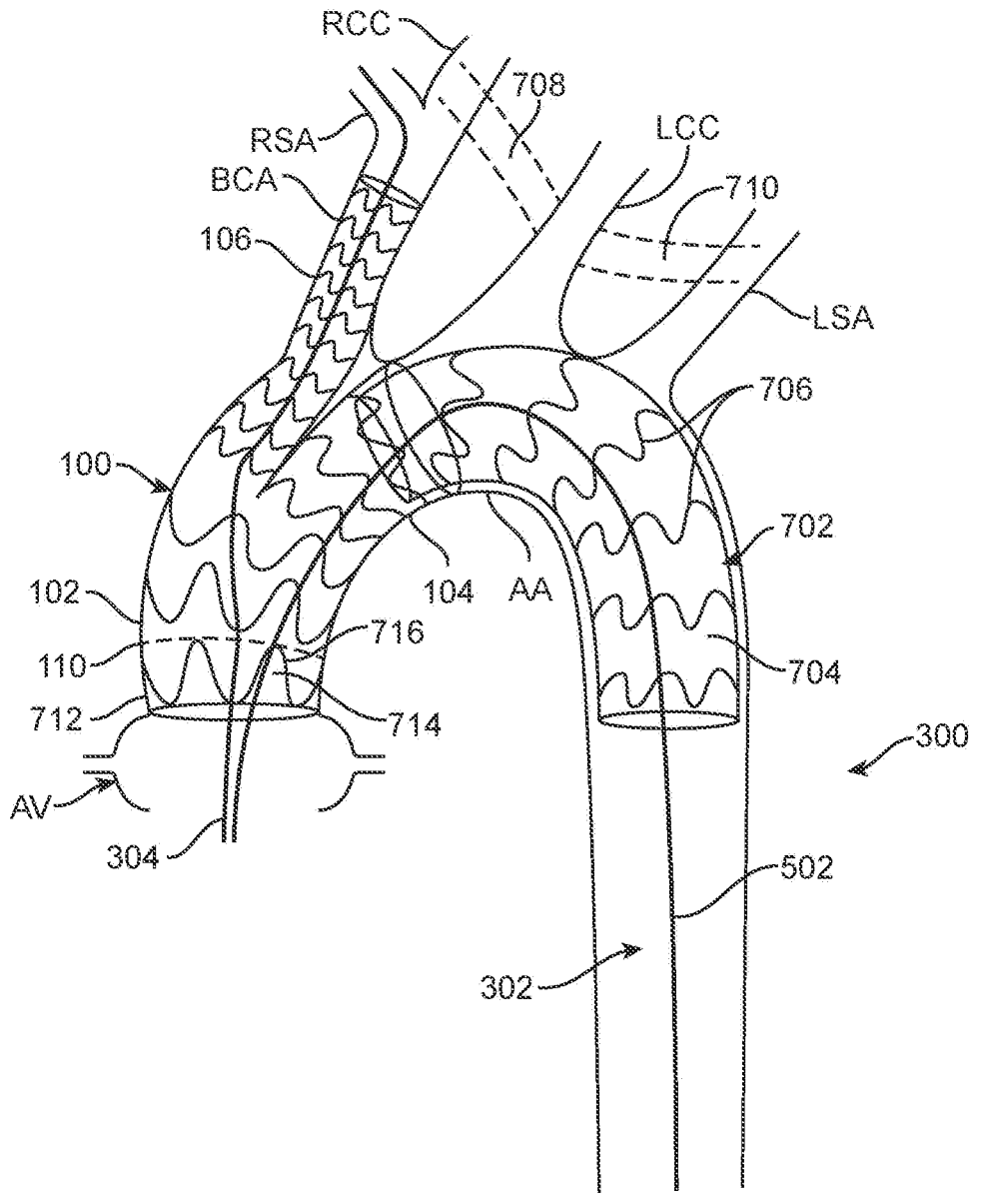
FIG. 7 is a cross-sectional view of the vessel assembly of FIG. 6 at a final stage during deployment of the tube graft into the modular stent device in accordance with one embodiment.

FIG. 7 is a cross-sectional view of vessel assembly 300 of FIG. 6 at a final stage during deployment of tube graft 702 into modular stent device 100 in accordance with one embodiment. Referring to FIGS. 6 and 7 together, sheath 604 of tube graft delivery system 602 is completely withdrawn to expose the entirety of tube graft 702. Upon being exposed, tube graft 702 self expands (or is balloon expanded) into bypass gate 104 and the aorta 302 and is attached thereto. Circumferential stents 134 of bypass gate 104 maximize fixation with tube graft 702.

Tube graft 702 includes graft material 704 and one or more circumferential stents 706. Graft material 704 includes any one of the graft materials as discussed above in relation to graft materials 126, 132, 138. In addition, circumferential stents 706 are similar to or identical to anyone of circumferential stents 128, 134, 140 as discussed above.

Upon completion of deployment of tube graft 702, blood flows through bypass gate 104 and tube graft 702 thus perfusing the distal territories. At the same time, bypass gate 104 and tube graft 702 exclude any overlapped diseased regions of the aorta 302.

In accordance with this embodiment, tube graft 702 overlaps, excludes and thus occludes the left common carotid artery LCC and the left subclavian artery LSA. In accordance with this embodiment, first and second bypasses 708, 710 provide perfusion to the left common carotid artery LCC and the left subclavian artery LSA. Illustratively, bypass 708 provides perfusion of the left common carotid artery LCC from the brachiocephalic artery BCA (or the right common carotid artery RCC). Bypass 710 provides perfusion of the left subclavian artery LCA from the left common carotid artery LCC.

Bypasses 708, 710 are surgically inserted during the same procedure as deployment of modular stent device 100 and tube graft 702. However, in another embodiment, bypasses 708, 710 are surgically inserted prior to deployment of modular stent device 100 and tube graft 702, e.g., to simplify the procedure.

In one embodiment, tube graft 702 is unnecessary and not deployed. For example, modular stent device 100 provide sufficient exclusion of the diseased region of the aorta 302. For example, modular stent device 100 is deployed as a standalone device to stabilize nonsurgical/high risk retrograde type A aortic dissection (RTAD) patients. Accordingly, tube graft 702 is unnecessary and not deployed. In the case where tube graft 702 is not deployed, perfusion is maintained to the left common carotid artery LCC and the left subclavian artery LSA and thus bypasses 708, 710 are unnecessary.

However, 40 to 60% of RTAD patients will need additional treatment in the descending thoracic aorta 302. In one embodiment, tube graft 702 is deployed when needed, e.g., at a period of time, e.g., months or years, after deployment of modular step device 100.

In another embodiment, other great vessel perfusion devices are used to provide perfusion to the left common carotid artery LCC and/or the left subclavian artery LSA and thus bypasses 708 and/or 710 are unnecessary. Examples of other great vessel perfusion devices are set forth in co-filed and commonly assigned U.S. patent application Ser. No. 16/367,906, entitled "SUPRA AORTIC ACCESS MODULAR STENT ASSEMBLY AND METHOD", of Perkins et al. and U.S. patent application Ser. No. 16/367,922, entitled "FEMORAL AORTIC ACCESS MODULAR STENT ASSEMBLY AND METHOD", of Perkins et al., which are both herein incorporated by reference in their entireties.

Further, as illustrated in FIG. 7, optionally, a proximal cuff 712 can be coupled to main body 102 and extend proximately therefrom. For example, proximal cuff 712 is deployed in the event that proximal end 110 of main body 102 is deployed distally from the aortic valve AV to extend between the desired deployment location and proximal end 110 of main body 102. Proximal cuff 712 is optional and in one embodiment is not deployed or used.

Proximal cuff 712 includes graft material 714 and one or more circumferential stents 716. Graft material 714 includes any one of the graft materials as discussed above in relation to graft materials 126, 132, 138. In addition, circumferential stents 716 are similar to or identical to anyone of circumferential stents 128, 134, 140 as discussed above.

Guidewires 304, 502 are removed if not previously removed to complete the procedure.

Figure 8:
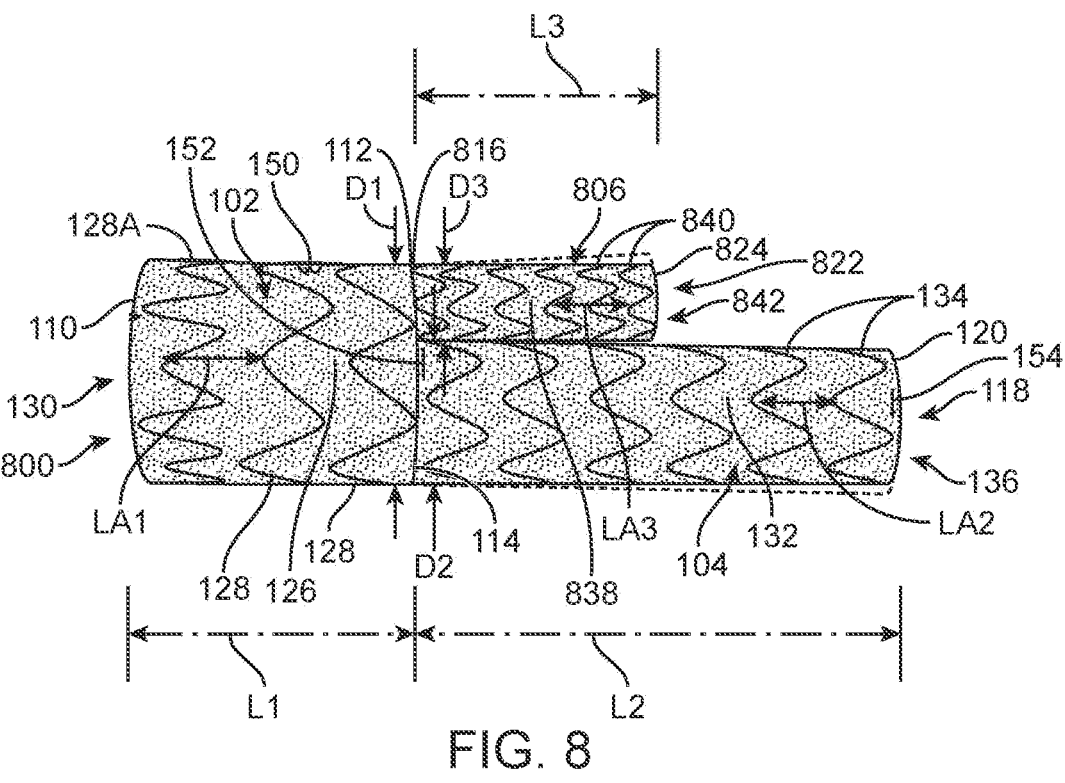
FIG. 8 is a side plan view of a modular stent device in accordance with another embodiment.
Figure 9:
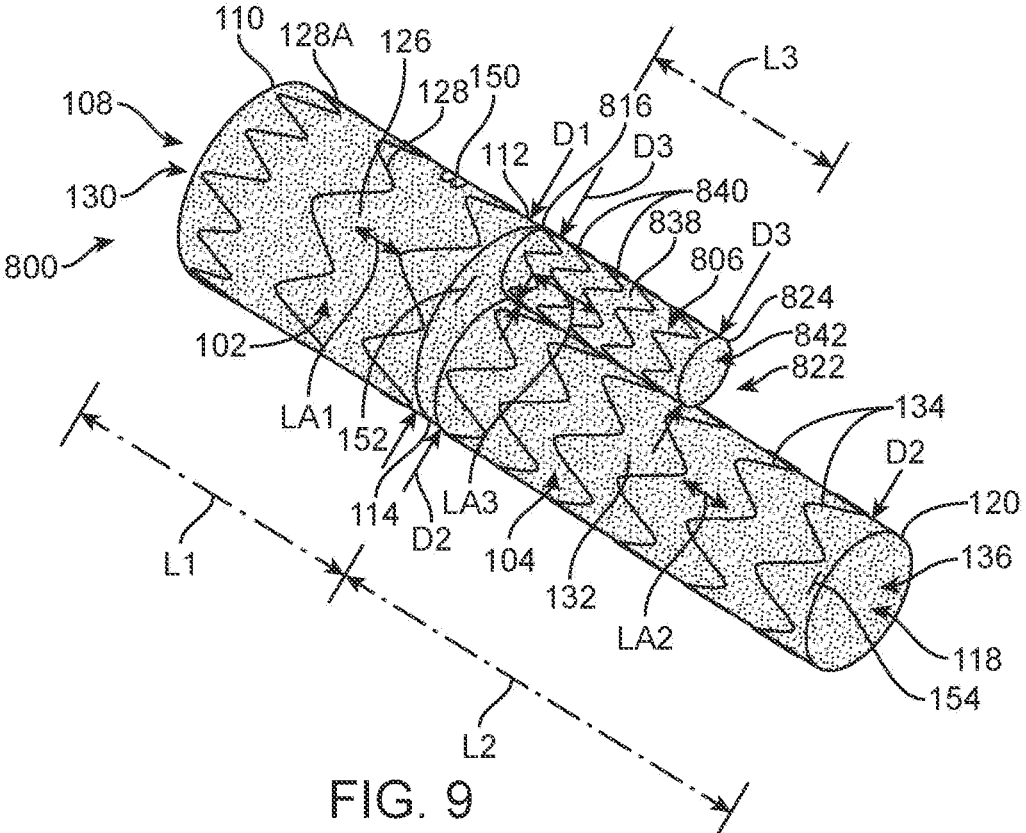
FIG. 9 is a perspective view of the modular stent device of FIG. 8 in accordance with one embodiment.

FIG. 8 is a side plan view of a modular stent device 800 in accordance with another embodiment. FIG. 9 is a perspective view of modular stent device 800 of FIG. 8 in accordance with one embodiment. Modular stent device 800 of FIGS. 8 and 9 is similar to modular stent device 100 of FIGS. 1 and 2 and only the significant differences are discussed below.

Referring now to FIGS. 8 and 9 together, modular stent device 800, sometimes called a prosthesis or aortic arch prosthesis, includes main body 102, bypass gate 104 and an artery leg 806.

In accordance with this embodiment, distal end 112 of main body 102 is coupled to proximal end 114 of bypass gate 104 and a proximal end 816 of artery leg 806.

Artery leg 806 includes a leg distal opening 822 at a distal end 824 of artery leg 806. Opening 822 is sometime called a distal second opening 822.

Artery leg 806 includes graft material 838 one or more circumferential stents 840 coupled to graft material 838. Graft material 838 may be any suitable graft material, for example and not limited to, woven polyester, DACRON® material, expanded polytetrafluoroethylene, polyurethane, silicone, electro spun materials, or other suitable materials.

Circumferential stents 840 may be coupled to graft material 838 using stitching or other means. In the embodiment shown in FIGS. 8 and 9, circumferential stents 840 are coupled to an outside surface of graft material 838. However, circumferential stents 840 may alternatively be coupled to an inside surface of graft material 838.

Although shown with a particular number of circumferential stents 840, in light of this disclosure, those of skill in the art will understand that artery leg 806 may include a greater or smaller number of stents 840, e.g., depending upon the desired length of artery leg 806 and/or the intended application thereof.

Circumferential stents 840 may be any stent material or configuration. As shown, circumferential stents 840, e.g., self-expanding members, are preferably made from a shape memory material, such as nickel-titanium alloy (nitinol), and are formed into a zig-zag configuration. The configuration of circumferential stents 840 is merely exemplary, and circumferential stents 840 may have any suitable configuration, including but not limiting to a continuous or non-continuous helical configuration. In another embodiment, circumferential stents 840 are balloon expandable stents.

Further, artery leg 806 includes longitudinal axis LA3. A lumen 842 is defined by graft material 838, and generally by artery leg 806. Lumen 842 extends generally parallel to longitudinal axis LA3 and between proximal end 816 and distal opening 822 of artery leg 806. Graft material 838 is cylindrical having a substantially uniform diameter in this embodiment. However, in other embodiments, graft material 838 varies in diameter.

Generally, main body 102 is bifurcated at distal end 112 into bypass gate 104 and artery leg 806. More particularly, lumen 130 of main body 102 is bifurcated into lumen 136 of bypass gate 104 and lumen 842 of artery leg 806. In one embodiment, graft materials 126, 132, 838 may be the same graft material, e.g., may be a single piece of graft material cut and sewn. However, in other embodiments, one or more of graft materials 126, 132, 838 may be different that the others of graft materials 126, 132, 838, e.g., different graft materials are cut and sewn together. In the relaxed configuration (unstressed) of modular stent device 800 as illustrated in FIGS. 8 and 9, longitudinal axes LA1, LA2, and LA3 are parallel with one another such that bypass gate 104 and artery leg 806 extend distally from main body 102.

Main body 102 has first diameter D1, bypass gate 104 has second diameter D2, and artery leg 806 has third diameter D3. In accordance with this embodiment, first diameter D1 is greater than second diameter D2. Further, second diameter D2 is greater than third diameter D3. In accordance with this embodiment, first diameter D1 is greater than second diameter D2 combined with third diameter D3 (D1>D2+D3) such that bypass gate 104 and artery leg 806 are located within an imaginary cylinder defined by graft material 126 of main body 102 extended in the distal direction. The parallel design mimics anatomical blood vessel bifurcations to limit flow disruptions.

In one embodiment, first diameter D1 is greater than second diameter D2 combined with third diameter D3 (D1>D2+D3) at distal end 112 and proximal ends 114, 816, sometimes called the transition region. However, main body 102, bypass gate 104 and/or artery leg 806, flare or taper away from the transition region in accordance with one embodiment, so D1>D2+D3 at the transition region but is not necessarily correct in regions away from the transition region. Flaring is indicated by the dashed lines in FIG. 8.

Stated another way, the transition region from main body 102 to artery leg 806 and bypass gate 104 does not exceed first diameter D1 of main body 102. This insures artery leg 806 and bypass gate 104 don't crush each other or negatively impact flow in any way. By avoiding having artery leg 806 and bypass gate 104 extend out wider than main body 102, a good seal of stents 128 of main body 102 against the aorta is insured and type I endoleaks are minimized or avoided.

In accordance with one embodiment, the transition region between main body 102 and artery leg 806 and bypass gate 104 is fully supported by one or more supporting stents, e.g., stents 128, 134, 840, to prevent kinking in angled anatomy. Absent the supporting stents, modular stent device 800 may be predispose to kinking in type III arches or gothic arches.

Main body 102 has a first length L1 in a direction parallel to the longitudinal axis LA1, bypass gate 104 has a second length L2 in a direction parallel to the longitudinal axis LA2, and artery leg 806 has a third length L3 in a direction parallel to the longitudinal axis LA3. In accordance with this embodiment, third length L3 is less than second length L2 such that distal opening 822 of artery leg 806 is proximal to distal opening 118 of bypass gate 104. Generally, artery leg 806 is shorter than bypass gate 104.

Artery leg 806 is configured to exert a higher radial force than the radial force of bypass gate 104. The radial force of bypass gate 104 is configured to be lower than that of artery leg 806 order to avoid collapse of artery leg 806 when bypass gate 104 is deployed against and adjacent thereof and thus maintain perfusion of the brachiocephalic artery as discussed further below.

To configure bypass gate 104 and artery leg 806 with differing relative radial forces, circumferential stents 840 of artery leg 806 be constructed with relatively thicker and/or shorter segments of material than circumferential stents 134 of bypass gate 104. Shorter and/or thicker circumferential stents 840 have less flexibility but greater radial force to ensure that circumferential stents 134 of bypass gate 104 do not collapse lumen 842 of artery leg 806. Other variations or modification of circumferential stents 134, 840 may be used to achieve relative radial forces in other embodiments.

Modular stent device 800 includes radiopaque markers 150, 152, 154. In accordance with this embodiment, radiopaque marker 150 is shaped as a figure 8 marker, i.e., in the shape of the number 8. Radiopaque marker 150 is sewn into graft material 126 in line with artery leg 806. Under fluoroscopy, radiopaque marker 150 is rotated so that it is seen on the edge on the outer curvature of the aortic arch in one embodiment so that artery leg 806 is accurately and reproducibly deployed on the outer curve of the aorta.

Figures 10, 11:
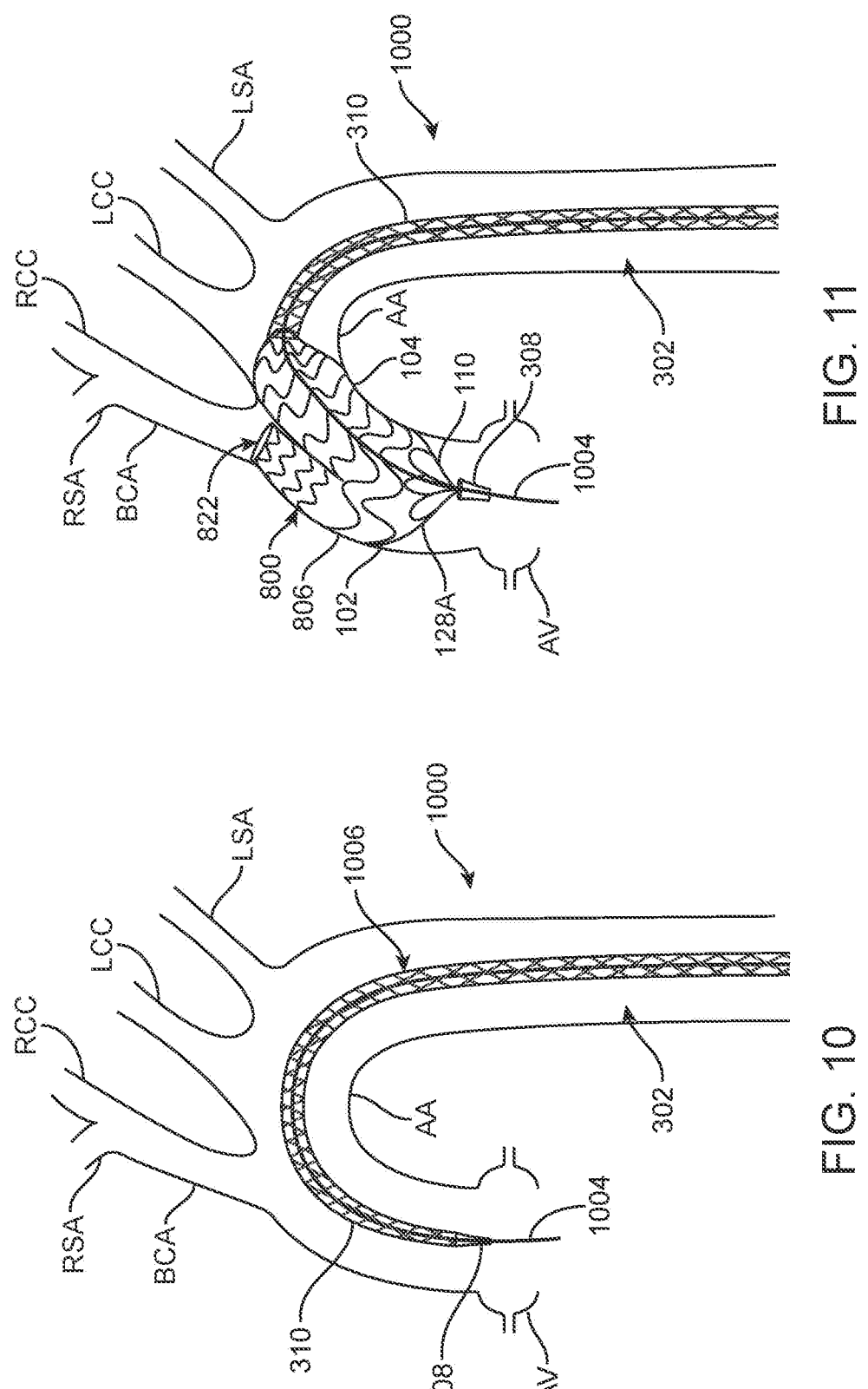
FIG. 10 is a cross-sectional view of a vessel assembly including the modular stent device of FIGS. 8 and 9 during deployment in accordance with one embodiment.
FIG. 11 is a cross-sectional view of the vessel assembly of FIG. 10 at a later stage during deployment of the modular stent device in accordance with one embodiment.

FIG. 10 is a cross-sectional view of a vessel assembly 1000 including modular stent device 800 of FIGS. 8 and 9 during deployment in accordance with one embodiment. Vessel assembly 1000 of FIG. 10 is similar to vessel assembly 300 of FIG. 3 and only the significant differences are discussed below.

Referring now to FIGS. 8, 9, and 10 together, a guide wire 1004 is introduced via femoral access. In one particular embodiment, guidewire 1004 is inserted into the femoral artery and routed up through the abdominal aorta, and into the thoracic aorta.

A delivery system 1006 including modular stent device 800 is introduced via femoral access and is advanced into the ascending aorta 302 over guidewire 1004. Delivery system 1006 is positioned at the desired location such that the position of modular stent device 800 is in the ascending aorta near the aortic valve AV.

In accordance with this embodiment, delivery system 1006 includes tip capture mechanism 308 and delivery sheath 310. Delivery sheath 310 maintains modular stent device 800 in a collapsed configuration during delivery to the desired location within the aorta 302. Tip capture mechanism 308 captures proximal end 110 of main body 102, e.g., proximal circumferential stent 128A, and keeps proximal end 110 in a collapsed configuration until released.

FIG. 11 is a cross-sectional view of vessel assembly 1000 of FIG. 10 at a later stage during deployment of modular stent device 800 in accordance with one embodiment. Referring now to FIGS. 10 and 11 together, delivery sheath 310 is withdrawn to expose main body 102, artery leg 806, and the proximal most portion of bypass gate 104. This deploys main body 102 and artery leg 806. Artery leg 806 is opened thus insuring perfusion to distal territories, e.g., including the brachiocephalic artery BCA. In accordance with this embodiment, distal opening 822 of artery branch 806 is proximal to the brachiocephalic artery BCA allowing easy cannulation thereof as discussed below.

To allow adjustment of the position of modular stent device 800, proximal end 110 of main body 102 remains captured within tip capture mechanism 308 and the distal portion of bypass gate 104 remains collapsed and captured within delivery sheath 310. Modular stent device 800 is moved, e.g., proximally or distally and/or rotated, if necessary, until positioned at the desired location.

Figures 12, 13:
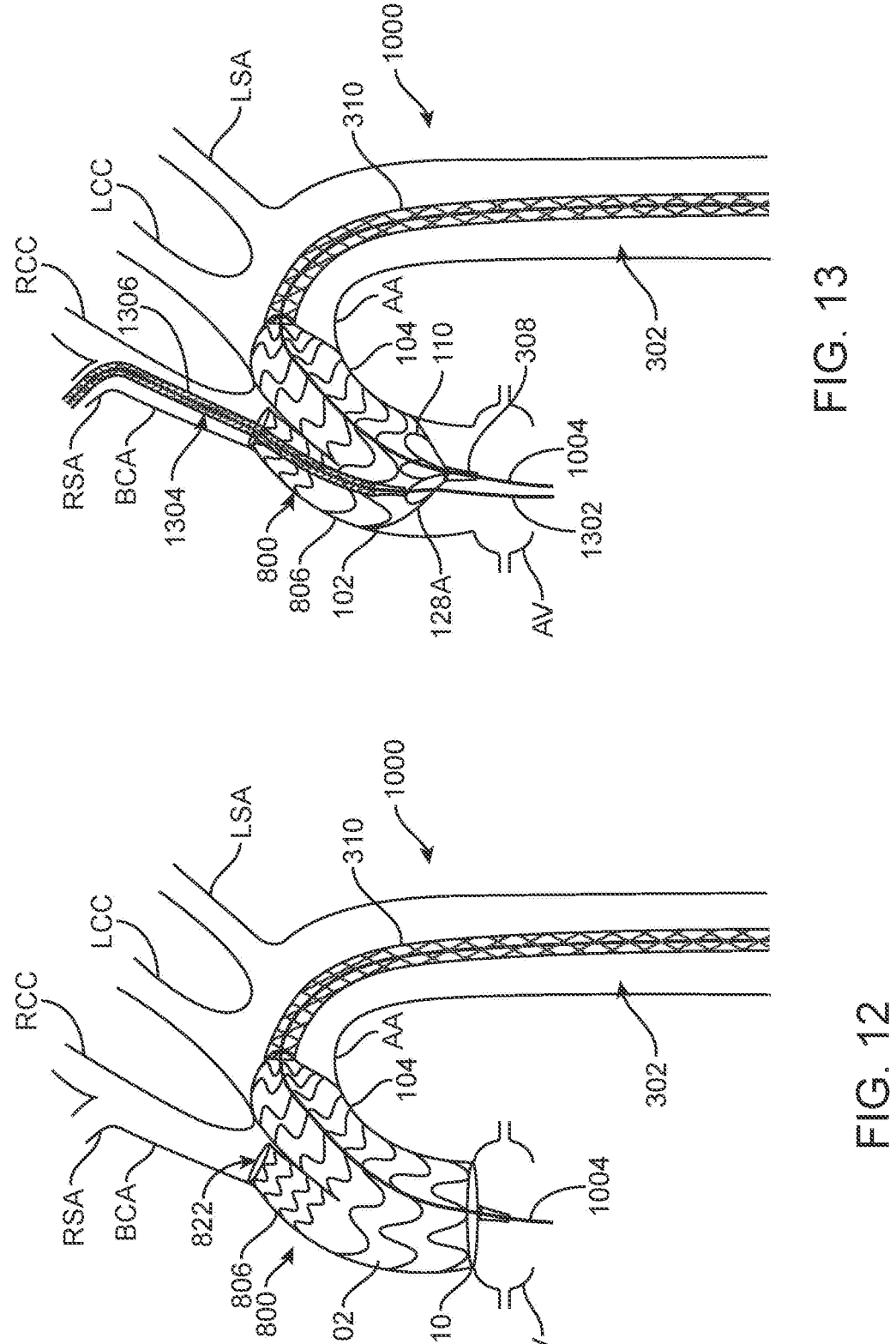
FIG. 12 is a cross-sectional view of the vessel assembly of FIG. 11 at a later stage during deployment of the modular stent device in accordance with one embodiment.
FIG. 13 is a cross-sectional view of the vessel assembly of FIG. 11 at a later stage during deployment of the modular stent device in accordance with another embodiment.

FIG. 12 is a cross-sectional view of vessel assembly 1000 of FIG. 11 at a later stage during deployment of modular stent device 800 in accordance with one embodiment. Referring to FIGS. 11 and 12 together, proximal end 110 of main body 102 is released from tip capture mechanism 308 and thus expands into aorta 302. However, in another embodiment, proximal end 110 of main body 102 remains captured within tip capture mechanism 308 at this stage of deployment, for example, as illustrated in FIG. 13.

FIG. 13 is a cross-sectional view of vessel assembly 1000 of FIG. 11 at a later stage during deployment of modular stent device 800 in accordance with another embodiment. Referring now to FIG. 13, proximal end 110 of main body 102 remains captured within tip capture mechanism 308 in accordance with this embodiment. Further, the distal portion of bypass gate 104 remains collapsed and captured within delivery sheath 310. This allows control of modular stent device 800, e.g., to allow modular stent device 800 to be held in place or to have the position thereof adjusted.

A second guidewire 1302 is introduced via supra aortic access, e.g., through the right subclavian artery RSA, and advanced into the ascending aorta 302. More particularly, guidewire 1302 is passed into distal opening 822 of artery leg 806, through artery leg 806, through main body 102 and out of proximal opening 108 of main body 102. A bridging stent graft delivery system 1304 including a bridging stent graft is advanced via supra aortic access into the artery leg 806 over guidewire 1302.

Figure 14:
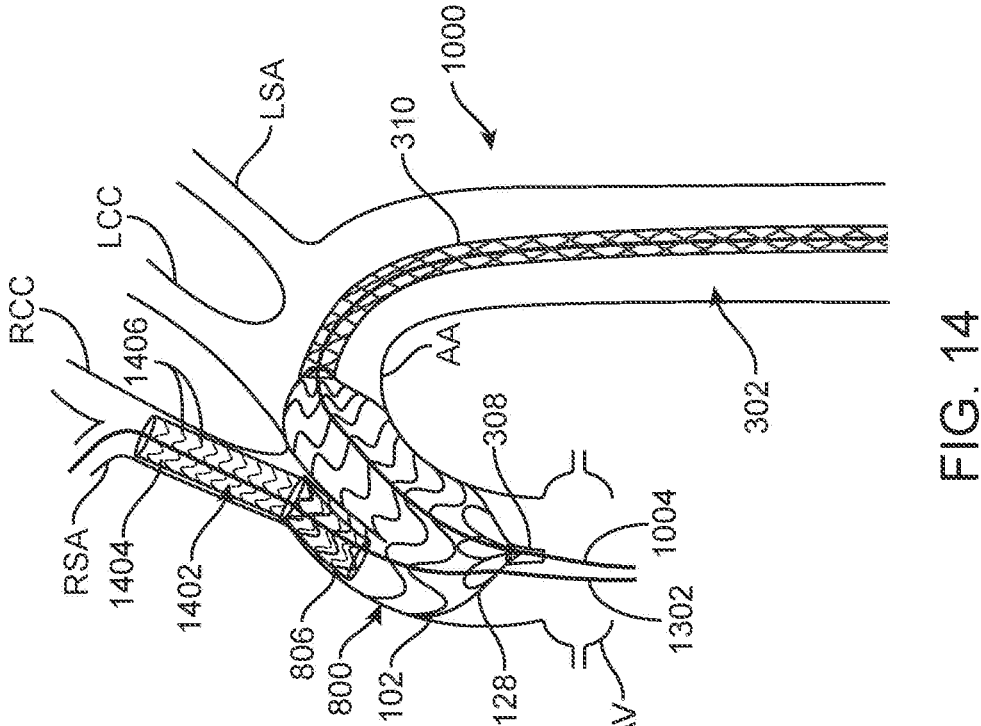
FIG. 14 is a cross-sectional view of the vessel assembly of FIG. 13 at a later stage during deployment of a bridging stent graft in accordance with another embodiment.

FIG. 14 is a cross-sectional view of vessel assembly 1000 of FIG. 13 at a later stage during deployment of a bridging stent graft 1402, sometimes called a bridging stent, in accordance with another embodiment. Referring to FIGS. 13 and 14 together, a delivery sheath 1306 (FIG. 13) of bridging stent graft delivery system 1304 is completely withdrawn to expose the entirety of bridging stent graft 1402. This deploys bridging stent graft 1402 within artery leg 806 and the brachiocephalic artery BCA. More particularly, bridging stent graft 1402 self-expands to be anchored within artery leg 806 and the brachiocephalic artery BCA.

Bridging stent graft 1402 includes graft material 1404 and one or more circumferential stents 1406. Upon deployment of bridging stent graft 1402, blood flow into artery leg 806 is bridged and passed into the brachiocephalic artery BCA through bridging stent graft 1402.

Figure 15:
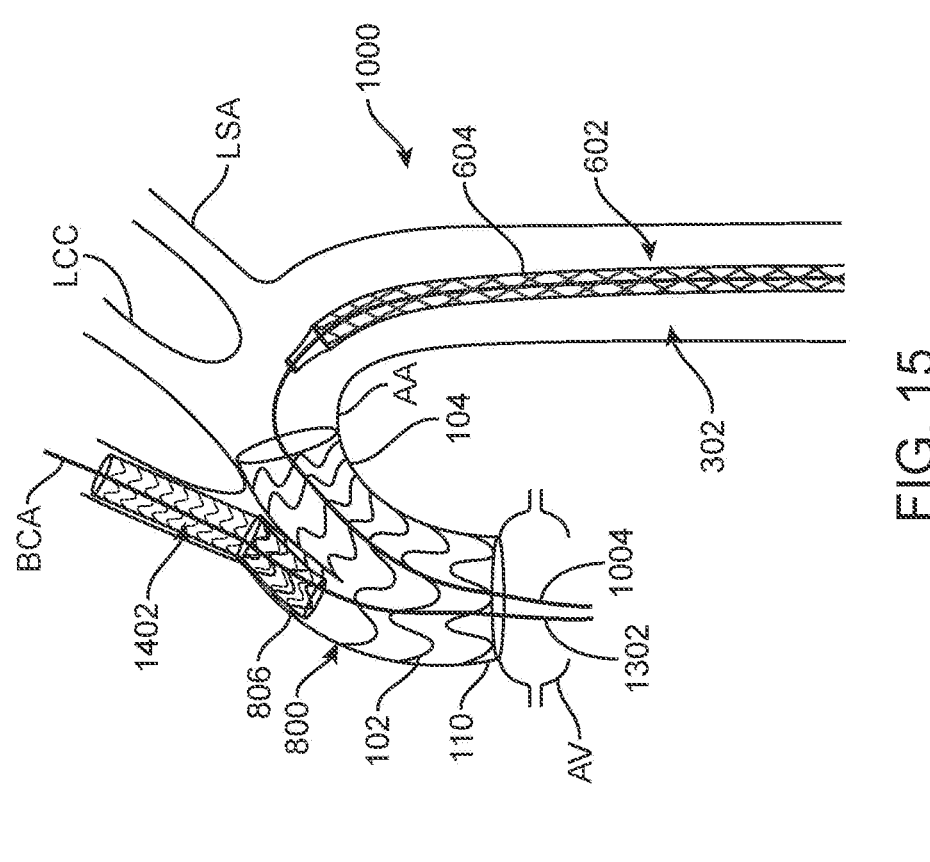
FIG. 15 is a cross-sectional view of the vessel assembly of FIG. 14 at a later stage during deployment of the modular stent device in accordance with one embodiment.

FIG. 15 is a cross-sectional view of vessel assembly 1000 of FIG. 14 at a later stage during deployment of modular stent device 800 in accordance with one embodiment. Referring to FIGS. 14 and 15 together, delivery sheath 310 (FIG. 14) of delivery system 1006 is completely withdrawn to expose the entirety of bypass gate 104. This deploys bypass gate 104 within the aorta 302. More particularly, bypass gate 104 self-expands to be anchored within the aorta 302.

As artery leg 806 has a greater radial force than bypass gate 104, artery leg 806 remains un-collapsed and opened. Accordingly, blood flow through artery leg 806 including bridging stent graft 1402 and perfusion of the brachiocephalic artery BCA is insured. This avoids stroke, or other medical complications from occlusion of the brachiocephalic artery BCA.

Perfusion of the brachiocephalic artery BCA is immediate and dependable. More particularly, artery leg 806 is released and opened during the initial deployment of modular stent device 800 thus insuring perfusion of the brachiocephalic artery BCA.

If there is any collapse between artery leg 806 and bypass gate 104, the collapse is in bypass gate 104. However, bypass gate 104 has a sufficiently large diameter D2 such that any collapse of bypass gate 104 is partial and blood flow through bypass gate 104 and aorta 302 is maintained.

Referring now just to FIG. 15, tube graft delivery system 602 is advanced over guidewire 1004 and into bypass gate 104. Tube graft delivery system 602 includes sheath 604.

Figure 16:
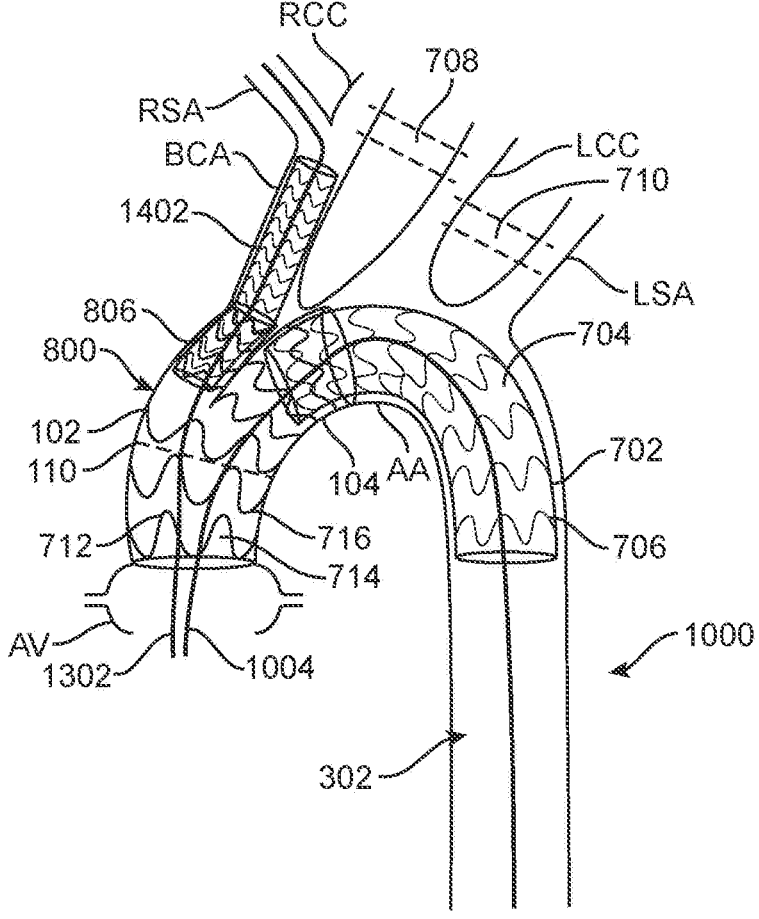
FIG. 16 is a cross-sectional view of the vessel assembly of FIG. 15 at a final stage during deployment of a tube graft into the modular stent device in accordance with one embodiment.

FIG. 16 is a cross-sectional view of vessel assembly 1000 of FIG. 15 at a final stage during deployment of tube graft 702 into modular stent device 800 in accordance with one embodiment. Referring to FIGS. 15 and 16 together, sheath 604 of tube graft delivery system 602 is completely withdrawn to expose the entirety of tube graft 702. Upon being exposed, tube graft 702 self-expands (or is balloon expanded) into bypass gate 104 and into aorta 302 and is attached thereto.

Tube graft 702 includes graft material 704 and one or more circumferential stents 706. Graft material 704 includes any one of the graft materials as discussed above in relation to graft materials 126, 132, 838. In addition, circumferential stents 706 are similar to or identical to anyone of circumferential stents 128, 134, 840 as discussed above.

Upon completion of tube graft 702, blood flows through bypass gate 104 and tube graft 702 thus perfusing the distal territories including the aorta 302. At the same time, bypass gate 104 and tube graft 702 exclude any overlapped diseased regions of the aorta 302.

In accordance with this embodiment, tube graft 702 overlaps, excludes and thus occludes the left common carotid artery LCC and the left subclavian artery LSA. In accordance with this embodiment, first and second bypasses 708, 710 provide perfusion to the left common carotid artery LCC and the left subclavian artery LSA. Illustratively, bypass 708 provides perfusion of the left common carotid artery LCC from the brachiocephalic artery BCA (or the right common carotid artery RCC). Bypass 710 provides perfusion of the left subclavian artery LCA from the left common carotid artery LCC.

Bypasses 708, 710 are surgically inserted during the same procedure as deployment of modular stent device 800 and tube graft 702. However, in another embodiment, bypasses 708, 710 are surgically inserted prior to deployment of modular stent device 800 and tube graft 702, e.g., to simplify the procedure.

In one embodiment, tube graft 702 is unnecessary and not deployed. For example, modular stent device 800 provide sufficient exclusion of the diseased region of the aorta 302. For example, modular stent device 800 including bridging stent graft 1402 are deployed as a standalone device to stabilize nonsurgical/high risk retrograde type A aortic dissection (RTAD) patients. Accordingly, tube graft 702 is unnecessary and not deployed. In the case where tube graft 702 is not deployed, perfusion is maintained to the left common carotid artery LCC and the left subclavian artery LSA and thus bypasses 708, 710 are unnecessary.

However, 40 to 60% of RTAD patients will need additional treatment in the descending thoracic aorta 302. In one embodiment, tube graft 702 is deployed when needed, e.g., at a period of time, e.g., months or years, after deployment of modular stent device 800.

In another embodiment, other great vessel perfusion devices are used to provide perfusion to the left common carotid artery LCC and/or the left subclavian artery LSA and thus bypasses 708 and/or 710 are unnecessary. Examples of other great vessel perfusion devices are set forth in co-filed and commonly assigned U.S. patent application Ser. No. 16/367,906, entitled "SUPRA AORTIC ACCESS MODULAR STENT ASSEMBLY AND METHOD", of Perkins et al. and U.S. patent application Ser. No. 16/367,922, entitled "FEMORAL AORTIC ACCESS MODULAR STENT ASSEMBLY AND METHOD", of Perkins et al., which are both herein incorporated by reference in their entireties.

Further, as illustrated in FIG. 16, optionally, a proximal cuff 712 can be coupled to main body 102 and extend proximately therefrom. For example, proximal cuff 712 is deployed in the event that proximal end 110 of main body 102 is deployed distally from the aortic valve AV to extend between the desired deployment location and proximal end 110 of main body 102. Proximal cuff 712 is optional and in one embodiment is not deployed or used.

Proximal cuff 712 includes graft material 714 and one or more circumferential stents 716. Graft material 714 includes any one of the graft materials as discussed above in relation to graft materials 126, 132, 838. In addition, circumferential stents 716 are similar to or identical to anyone of circumferential stents 128, 134, 840 as discussed above.

Guidewires 1004, 1302 are removed if not previously removed to complete the procedure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An assembly comprising:
   a modular stent device comprising:
      a main body having a proximal end and a distal end, the main body having a main body diameter extending from the proximal end to the distal end of the main body;
      a bypass gate having a proximal end and a distal end, the bypass gate continuously extending distally from the distal end of the main body;
      an artery leg having a proximal end and a distal end, the artery leg having an artery leg diameter extending from the proximal end to the distal end of the artery leg, the artery leg extending distally from the distal end of the main body; and
      a transition region where the main body meets the bypass gate and the artery leg,
   wherein the proximal ends of the bypass gate and the artery leg contact in the transition region, the proximal end of the bypass gate and the distal end of the main body contact in the transition region, the proximal end of the artery leg and the distal end of the main body contact in the transition region radially opposite the contact of the proximal end of the bypass gate and the distal end of the main body in the transition region,
   wherein the modular stent device continuously extends distally from the proximal end of the main body to the distal end of the bypass gate or the artery leg,
   wherein the artery leg has a greater radial force than a radial force of the bypass gate,
   wherein the main body has a first longitudinal axis, the bypass gate has a second longitudinal axis, and the artery leg has a third longitudinal axis, the first, second, and third longitudinal axes are parallel with one another when the modular stent device is in a relaxed configuration, wherein a length of the artery leg is less than a length of the bypass gate.

2. The assembly of claim 1 wherein the length of the artery leg is measured along the third longitudinal axis, and the length of the bypass gate is measured along the second longitudinal axis.

3. The assembly of claim 1 further comprising a radiopaque marker in line with the artery leg.

4. The assembly of claim 1 further comprising a tip capture mechanism to control proximal deployment accuracy of the main body.

5. The assembly of claim 1 wherein the main body has a main body diameter, the bypass gate has a bypass gate diameter, the main body diameter being greater than the bypass gate diameter and the artery leg diameter together at the transition region.

6. The assembly of claim 5 wherein the bypass gate and the artery leg are located within an imaginary cylinder defined by the main body extended in a distal direction at the transition region.

7. The assembly of claim 5 wherein the bypass gate diameter is greater than the artery leg diameter at the transition region.

8. The assembly of claim 1 wherein stents of the artery leg have a greater radial force than stents of the bypass gate.

9. The assembly of claim 1 wherein the bypass gate is configured to collapse relative to the artery leg.

10. The assembly of claim 1 further comprising a tube graft coupled to the bypass gate and extending distally therefrom.

11. The assembly of claim 1 further comprising a proximal cuff coupled to the main body and extending proximally therefrom.

12. The assembly of claim 1 wherein the transition region includes a radiopaque marker.

13. The assembly of claim 1, wherein the bypass gate and the artery leg continuously extend distally from the distal end of the main body.

14. The assembly of claim 1, wherein the main body flares at a proximal end thereof.

15. The assembly of claim 1, wherein the bypass gate flares at a distal end thereof and the artery leg flares at a distal end thereof.

16. An assembly comprising:
a modular stent device comprising:
    a main body having a proximal end and a distal end, the distal end of the main body having a circular profile;
    a bypass gate having a proximal end and a distal end, the proximal end of the bypass gate having a circular profile, the bypass gate continuously extending distally from the distal end of the main body;
    an artery leg having a proximal end and a distal end, the proximal end of the artery leg having a circular profile, the artery leg having an artery leg diameter extending from the proximal end to the distal end of the artery leg, the artery leg extending distally from the distal end of the main body; and
    a transition region where the main body meets the bypass gate and the artery leg to form a first transition region surface and a second transition region surface spaced apart from the first transition region surface, the first transition region surface bounded by a first portion of the circular profile of the distal end of the main body, a first portion of the circular profile of the proximal end of the bypass gate, and a first portion of the circular profile of the proximal end of the artery leg, the second transition region surface bounded by a second portion of the circular profile of the distal end of the main body, a second portion of the circular profile of the proximal end of the bypass gate, and a second portion of the circular profile of the proximal end of the artery leg, the first portions of the circular profiles of the distal end of the main body and the proximal ends of the bypass gate and the artery leg are different than the second portions of the circular profiles of the distal end of the main body and the proximal ends of the bypass gate and the artery leg, wherein the modular stent device continuously extends distally from the proximal end of the main body to the distal end of the bypass gate or the artery leg, wherein the artery leg has a greater radial force than a radial force of the bypass gate, wherein the main body has a first longitudinal axis, the bypass gate has a second longitudinal axis, and the artery leg has a third longitudinal axis, the first, second, and third longitudinal axes are parallel with one another when the modular stent device is in a relaxed configuration, wherein a length of the artery leg is less than a length of the bypass gate.

17. The assembly of claim 16 wherein the bypass gate flares at a distal end thereof.

18. The assembly of claim 16 wherein the main body flares at a proximal end thereof.

19. The assembly of claim 16 wherein the bypass gate flares at a distal end thereof and the main body flares at a proximal end thereof.

20. An assembly comprising:
a modular stent device comprising:
    a main body having a proximal end and a distal end;
    a bypass gate having a proximal end and a distal end, the bypass gate continuously extending distally from the distal end of the main body to the distal end of the bypass gate without bifurcation, the bypass gate having a bypass gate diameter; and
    an artery leg having a proximal end and a distal end, the artery leg continuously extending distally from the distal end of the main body to the distal end of the artery leg without bifurcation, the artery leg having an artery leg diameter; and
    a transition region where the main body meets the bypass gate and the artery leg to form a closed transition region surface bounded by a bounding portion of the distal end of the main body, and the proximal ends of the bypass gate, and the artery leg, the bounding portion includes a main body/bypass gate contacting region where the distal end of the main body contacts the proximal end of the bypass gate, a bypass gate/artery leg contacting region where the proximal end of the bypass gate contacts the proximal end of the artery leg, and an artery leg/main body contacting region where the proximal end of the artery leg contacts the distal end of the main body, the main body/bypass gate, bypass gate/artery leg, and artery leg/main body contacting regions radially align, wherein the artery leg has a greater radial force than a radial force of the bypass gate, wherein the main body has a first longitudinal axis, the bypass gate has a second longitudinal axis, and the artery leg has a third longitudinal axis, the first, second, and third longitudinal axes are parallel with one another when the modular stent device is in a relaxed configuration, wherein a length of the artery leg is less than a length of the bypass gate.

* * * * *